United States Patent [19]

Feldman et al.

[11] Patent Number: 5,658,529
[45] Date of Patent: Aug. 19, 1997

[54] METHOD OF PROTECTING AND STERILIZING ALUMINUM SURFACES ON MEDICAL INSTRUMENTS

[75] Inventors: Leslie A. Feldman, Calabasas Hills; Henry Hui, Laguna Niguel, both of Calif.

[73] Assignee: Johnson & Johnson Medical, Inc., Arlington, Tex.

[21] Appl. No.: 614,705

[22] Filed: Mar. 13, 1996

[51] Int. Cl.$^6$ ............................................. A61L 2/08
[52] U.S. Cl. ...................... 422/23; 422/27; 422/29; 205/300
[58] Field of Search ................... 422/23, 27, 29; 205/300

[56] References Cited

U.S. PATENT DOCUMENTS

| | | | |
|---|---|---|---|
| 3,849,263 | 11/1974 | Gedde | 204/35 N |
| 3,850,054 | 11/1974 | Weissman | 76/108 R |
| 4,414,077 | 11/1983 | Yoshida et al. | 204/35 N |
| 4,643,876 | 2/1987 | Jacobs et al. | 422/23 |
| 5,087,418 | 2/1992 | Jacob | 422/23 |

*Primary Examiner*—Cynthia L. Nessler
*Attorney, Agent, or Firm*—Andrew C. Farmer

[57] ABSTRACT

A process for color anodizing and sterilizing aluminum surfaces on medical instruments without fading the anodized color comprises the steps of: anodizing an aluminum surface on a medical instrument to form an oxide film; immersing the surface in a salt bath of a coloring metal and electrolytically depositing the coloring metal onto the oxide film; and repeatedly sterilizing the medical instrument and its surface by exposing it to an oxidizing sterilant, whereby the electrolytically deposited coloring metal remains adhered to the surface and the color of the surface is not adversely affected by the repeated exposure to the oxidizing sterilant. Preferably, the sterilant comprises hydrogen peroxide, the coloring metal comprises tin and the surface remains noncytotoxic after the anodizing, coloring steps and sterilizing steps.

12 Claims, No Drawings

METHOD OF PROTECTING AND STERILIZING ALUMINUM SURFACES ON MEDICAL INSTRUMENTS

BACKGROUND

1. Field of the Invention

The present invention relates generally to medical instruments and to methods for applying protective coatings to aluminum surfaces of the medical instruments and sterilizing those surfaces.

2. State of the Prior Art

Medical instruments are sterilized in various fashions. Autoclaving, or steam sterilization, is used to sterilize instruments such as scalpels and the like. Many medical instruments contain components that cannot survive the intense heat of autoclaving. A popular method for sterilizing these instruments is hydrogen peroxide gas plasma sterilization such as the STERRAD Sterilization System available from Advanced Sterilization Products division of Johnson & Johnson Medical, Inc. Such systems comprise a sterilization chamber into which medical devices are placed for sterilization. A quantity of vapor phase hydrogen peroxide of relatively high concentration enters the chamber and penetrates all areas of the medical devices. After the hydrogen peroxide vapor is well dispersed throughout the chamber an electromagnetic field is applied which drives the hydrogen peroxide into the plasma phase and completes the sterilization procedure. After the electromagnetic field is removed, the particles in the plasma recombine as oxygen and water, leaving behind little or no toxic residue. Such a process is described in more detail by Jacobs et at. in U.S. Pat. No. 4,643,876, issued Feb. 17, 1987, and incorporated herein by reference.

Common black dyed or colored anodized aluminum coatings employed on medical devices are fabricated by an anodization step to build up an oxide layer on the aluminum surface, followed by immersion in a dye bath. The dye is absorbed into the film, which is then sealed by immersion in boiling water or a chemical sealing bath. Heretofore, it was not thought possible to sterilize such instruments using hydrogen peroxide gas plasma sterilization due to fading of black or colored anodized coatings that was observed on certain aluminum devices or components that have been so sterilized.

We have found that the fading of anodized coatings in such an environment appears to be caused by exposure to the hydrogen peroxide vapor itself, and is probably not due to any effects of the plasma. The anodized coatings of medical devices comprise an oxide layer on the surface of the aluminum. The color comes from organic dyes in this anodic oxide layer. The hydrogen peroxide only affects the dye. While the dye in the surface fades after exposure to hydrogen peroxide vapor over a number of process cycles, the anodic oxide layer remains intact. This has been demonstrated by electrical resistance measurements, which showed no change in high surface resistance values between the original black coating and one which had lost its color. This indicates that the protective oxide layer has remained intact. Thus, the fading does not appear to have any adverse consequences which affect the functionality or effectiveness of the devices. However, the loss of color on the surface may be an undesirable cosmetic change.

SUMMARY OF THE INVENTION

To overcome this problem, we have discovered that inorganic coloring agents electrolytically applied to the oxide layer provide an attractive appearance and appear to resist even repeated exposure to high concentrations of hydrogen peroxide.

A process according to the invention for color anodizing and sterilizing aluminum surfaces on medical instruments without fading the anodized color comprises the steps of: anodizing an aluminum surface on a medical instrument to form an oxide film; immersing the surface in a salt bath of a coloring metal and electrolytically depositing the coloring metal onto the oxide film; and repeatedly sterilizing the medical instrument and its surface by exposing it to an oxidizing sterilant, whereby the electrolytically deposited coloring metal remains adhered to the surface and the color of the surface is not adversely affected by the repeated exposure to the oxidizing sterilant. By the term aluminum, it is understood to include alloys of aluminum. Preferably, the sterilant comprises hydrogen peroxide, the coloring metal comprises tin and the surface remains non-cytotoxic after the anodizing, coloring steps and sterilizing steps. The hydrogen peroxide is present in an atmosphere of hydrogen peroxide vapor in a concentration of greater than 40%, preferably greater than 60%.

Anodizing with electrolytic coloring has been used for several decades to anodize architectural aluminum fixtures. First, anodization of aluminum, one of its alloys, or other light metal, produces a porous metal oxide film (porous anodic layer) on the metal under alternating or direct current flow in an electrolytic bath in which the metal is suspended. Many different organic and inorganic acids may be combined to create a great variety of electrolytes. Sulfuric acid is useful due to its availability, low cost, and low dissolving power.

In a subsequent electrocoloring step, an inorganic material, such as a metal, is deposited in the pores of the metal oxide film by the passage of an electric current. Alternating or direct current is passed between the anodized aluminum substrate and a counter-electrode. The counter-electrode can comprise graphite or stainless steel; although nickel, copper, and tin electrodes can also be used. The deposition of the inorganic material gives the anodized aluminum a colored appearance. A good discussion of a two step anodization/electrocoloring process is given by Gedde in U.S. Pat. No. 3,849,263, issued Nov. 19, 1974, and incorporated herein by reference.

Test Results

Testing showed a significant difference in color fastness between dyed and two-step anodized aluminum. Aluminum coupons of type 6063 were anodized by either a 1) a black dye process or 2) a two-step anodization employing electrolytic deposition of tin to produce a colored anodization.

In both processes, the coupons were first anodized in an aqueous solution of 95 mL/L $H_2SO_4$ for 30 minutes with a direct current of 15 to 21 volts and at a density of 9 to 12 A/sq. ft. In the dye process, the coupons were then immersed in a bath of organic dye and sealed in a sealing bath. In the two-step process, the coupons were electrocolored in an aqueous solution of 10 mL/L $H_2SO_4$, 20 g/L $SnSO_4$, and 10 mL/L phenol sulphonic acid. The coloring step was carried out at 20° to 24° C. with a direct current of 10 to 18 volts and at a current density of 2 to 10 A/Sq. Ft. Coloring times range from 10 seconds for a light bronze to 15 minutes for a deep black finish. Following the electrocoloring step, the coupons were sealed in an aqueous solution of Ni acetate (5–5.8 g/L) for 30 minutes.

Each coupon was subjected 100 cycles in a STERRAD hydrogen peroxide gas plasma sterilizer. Each cycle first subjected the coupons to a vacuum, whereupon a 59% solution of hydrogen peroxide is injected into the sterilization chamber which vaporizes and diffuses throughout the chamber for about ¾ of an hour at a concentration of approximately 6 mg/L. An electromagnetic field is then applied which excites the hydrogen peroxide into the plasma state of matter. This is continued for 15 to 20 minutes. The chamber is then vented.

The dye colored coupons anodized by the first method faded to clear within a few cycles. However, even after 100 cycles, they retained their original electrical resistivity. The electrocolored coupons anodized by the second method remained dark black in color after 100 cycles, and also, of course, retained their electrical resistivity.

Initial results comparing the rates of decomposition of liquid hydrogen peroxide in solution by both black dyed anodized and two-step anodized aluminum indicated that both decomposition rates are low and approximately the same. According to the literature on hazardous chemicals, elemental tin is non-toxic. Samples of both dyed and two-step anodized 6063 aluminum coupons (4×6×0.125 in.) were evaluated for toxicity. Results of cytotoxicity testing were negative (nontoxic) for both anodized coatings. In the tests, a monolayer of L-929 cells was grown to confluency and exposed to an extract of the test article prepared by placing the test article in 108 ml of 5% Minimum Essential Medium at 37° C. for periods of 24 to 72 hours. At the end of the tests the cells were examined for presence of the confluent monolayer, vacuolization, cellular swelling, crenation and cellular lysis. In all tests the confluent monolayer was present and substantially no vacuolization, cellular swelling, crenation or cellular lysis were detected.

While the invention has been particularly described in connection with specific embodiments thereof, it is to be understood that this is by way of illustration and not of limitation, and that the scope of the appended claims should be construed as broadly as the prior art will permit. For instance the concepts of this invention may be applied to other metals susceptible to anodizing such as titanium, magnesium, molybdenum, tungsten and alloys thereof.

What is claimed is:

1. A process for color anodizing and sterilizing aluminum surfaces on medical instruments without fading the anodized color comprises the steps of:

anodizing an aluminum surface on a medical instrument to form an oxide film;

immersing the surface in a salt bath of a coloring metal and electrolytically depositing the coloring metal onto the oxide film; and repeatedly sterilizing the medical instrument and its surface by exposing it to an oxidizing sterilant, whereby the electrolytically deposited coloring metal remains adhered to the surface and the color of the surface is not adversely affected by the repeated exposure to the oxidizing sterilant.

2. A process according to claim 1 wherein the step of exposing the medical instrument and its surface to an oxidizing sterilant comprises subjecting the medical instrument and its surface to an atmosphere of hydrogen peroxide vapor.

3. A process according to claim 2 wherein the concentration of hydrogen peroxide in the atmosphere of hydrogen peroxide vapor is greater than 60%.

4. A process according to claim 2 wherein the concentration of hydrogen peroxide in the atmosphere of hydrogen peroxide vapor is greater than 40%.

5. A process according to claim 4 wherein the step of sterilizing the medical instrument and its surface further comprises the step of exposing the medical instrument and surface to a plasma phase formed of hydrogen peroxide.

6. A process according to claim 2 wherein the step of sterilizing the medical instrument and its surface is repeated at least 10 times and thereafter the color of the surface is not adversely affected.

7. A process according to claim 2 wherein the step of sterilizing the medical instrument and its surface is repeated at least 100 times and thereafter the color of the surface is not adversely affected.

8. A process according to claim 2 wherein the coloring metal comprises tin.

9. A process according to claim 2 wherein the surface remains non-cytotoxic after the anodizing and coloring steps.

10. A process according to claim 9 wherein the surface remains non-cytotoxic after the sterilization steps.

11. A process according to claim 1 wherein the surface remains non-cytotoxic after the anodizing and coloring steps.

12. A process according to claim 11 wherein the surface remains non-cytotoxic after the sterilization steps.

* * * * *